United States Patent [19]

Goebel et al.

[11] Patent Number: 5,260,470

[45] Date of Patent: Nov. 9, 1993

[54] METHOD OF PURIFYING ALKOXYSILANES

[75] Inventors: Thomas Goebel, Hanau; Peter Panster, Rodenbach; Werner Will, Gelnhausen-Hoechst; Peter Kleinschmit, Hanau, all of Fed. Rep. of Germany

[73] Assignee: Degussa Aktiengesellschaft, Frankfurt am Main, Fed. Rep. of Germany

[21] Appl. No.: 939,470

[22] Filed: Sep. 2, 1992

[30] Foreign Application Priority Data

Sep. 14, 1991 [DE] Fed. Rep. of Germany ....... 4130643

[51] Int. Cl.$^5$ .............................. C07F 7/08; C07F 7/18
[52] U.S. Cl. ...................................... 556/466; 556/467
[58] Field of Search .............. 556/466, 467, 484, 446, 556/476; 528/30

[56] References Cited

U.S. PATENT DOCUMENTS

| | | | |
|---|---|---|---|
| 4,362,885 | 12/1982 | Panster et al. | 556/446 |
| 4,410,669 | 10/1983 | Panster et al. | 525/474 |
| 4,424,332 | 1/1984 | Panster et al. | 528/30 |
| 4,455,415 | 6/1984 | Panster et al. | 528/39 |
| 4,552,700 | 11/1985 | Panster et al. | 556/9 |
| 4,595,740 | 6/1986 | Panster | 528/30 |
| 4,645,847 | 2/1987 | Panster et al. | 556/9 |
| 4,645,848 | 2/1987 | Panster et al. | 556/9 |
| 4,647,644 | 3/1987 | Panster et al. | 528/30 |
| 4,647,679 | 3/1987 | Panster et al. | 556/9 |
| 4,647,682 | 3/1987 | Panster et al. | 556/431 |
| 4,845,163 | 7/1989 | Panster et al. | 525/475 |
| 4,885,470 | 8/1989 | Panster et al. | 556/421 |
| 4,954,599 | 9/1990 | Panster et al. | 528/38 |
| 4,956,486 | 9/1990 | Marko et al. | 536/466 |
| 4,962,221 | 10/1990 | Huntress et al. | 556/466 X |
| 4,999,413 | 3/1991 | Panster et al. | 528/30 |
| 5,003,024 | 3/1991 | Panster et al. | 528/30 |
| 5,019,637 | 5/1991 | Panster | 528/25 |
| 5,061,773 | 10/1991 | Panster et al. | 528/9 |
| 5,093,451 | 3/1992 | Panster et al. | 528/9 |
| 5,094,831 | 3/1992 | Klockner et al. | 423/342 |
| 5,104,999 | 4/1992 | Satoh | 556/466 |
| 5,126,473 | 6/1992 | Klockner et al. | 556/473 |
| 5,130,396 | 7/1992 | Panster et al. | 528/9 |
| 5,132,337 | 7/1992 | Panster et al. | 523/117 |

*Primary Examiner*—Arthur C. Prescott
*Attorney, Agent, or Firm*—Beveridge, DeGrandi, Weilacher & Young

[57] ABSTRACT

A method of purifying alkoxysilanes contaminated by organosilicon compounds with hydrolyzable chlorine atoms is disclosed wherein the alkoxysilanes are reacted in a pressure reactor with an alcohol, preferably in the presence of an HCl acceptor, at a temperature of 5° C. to 160° C. above the boiling point of the alcohol used and at the pressure which develops in the reactor.

19 Claims, No Drawings

METHOD OF PURIFYING ALKOXYSILANES

BACKGROUND AND INVENTION

The present invention relates to a method of purifying alkoxysilanes of chlorine-containing impurities. Alkoxysilanes, especially with sterically demanding groups, are finding increasing interest in the fields of application of building protection and cable masses. The purity requirements as regards the acid, base and particularly the chloride content are extremely high, especially for organosilanes used in the cable industry.

Alkoxysilanes with the general formula $R_nSi(OR')_{4-n}$ are obtained by liquid-liquid, gas-liquid or gas-gas phase reaction of the corresponding chlorosilanes with alcohol. The raw products obtained after the esterification still contain a residual acid content which can be demonstrated analytically as HCl and which can be traced to certain components of the so-called "monochloro derivative" as a consequence of the incompletely performed conversion during the alcoholysis. Such a method is described e.g. in European Patent 421,644.

Chung and Hayes (Journal of Organometallic Chemistry (1984), 265: 135-139) describe a method for the removal of chlorine-containing impurities in alkoxysilanes using lithium aluminum hydride or metallic sodium. The hydrolyzable chlorine content was lowered to below 100 mg/kg only in the presence of sodium. It is known that alkali metals fall into the group of interfering substances and that these methods necessitate an extensive safety analysis when used on a large industrial scale and can cause safety problems In European Patent 0,223,210 there is described a purification method for organosilanes of the general formula $R_nSi(OR')_{4-n}$ with the terminal groups $R=C_{1-8}$. The method uses aoidic clays or iron chloride in which very low concentrations of chlorine-containing impurities are likewise achieved. This method operates at normal pressure and preferably at the boiling temperature of the alkoxysilane in question. However, a thermally induced condensation occurs thereby, especially in the presence of strong bases, depending on the structure of the organosilane. The alcohol which is freed in the course of the reaction lowers the treatment temperature. This generally results in prolonging the dwell time and, as a consequence of the silane formation, lower yield.

SUMMARY OF THE INVENTION

An object of the present invention is to provide a method for the purification of alkoxysilanes, especially with sterically demanding terminal groups, in which in addition to satisfactory yields, the total chlorine content can be lowered to distinctly below 150 mg/kg.

According to the present invention, this and other objects are achieved by a method of purifying alkoxysilanes contaminated by organosilicon compounds with hydrolyzable chlorine atoms. The alkoxysilanes are reacted in a pressure reactor with an alcohol, preferably in the presence of an HCl acceptor, at a temperature of 5° C. to 160° C., preferably 40 to 70° C. above the boiling point of the alcohol used and at the pressure which develops in the course of the reaction. The latter is generally 1 to 50 bars. The alcohol which corresponds to the alkoxy groups on the Si atom is preferably used. At least an alcohol concentration equivalent to the amount of the Cl to be hydrolyzed must be used, generally 5 to 40% by weight relative to the total mixture.

The temperature range as stated above should of course also be adjusted to the decomposition temperature of the alkoxysilane so that the reaction time can be in general between 5 min. and 48 h.

Thereafter, the precipitated chloride product formed in the above described method is separated off and a very pure alkoxysilane is obtained after the distilling off of the alcohol. The alkoxysilane contains less than 15 μg/g hydrolyzable chloride.

DETAILED DESCRIPTION OF THE INVENTION

The method can be utilized with alkoxysilanes of the general formula:

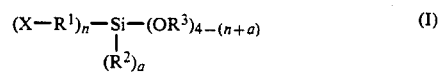

n=0, 1, 2
a=0, 1
in which
corresponds to an alkylene group with a chain length of $C_3-C_{20}$
  an alkenylene group (vinylene, propylene)
  an arylene group (phenylene, tolyl-, xylyl-)
  and/or aralkyl group (benzyl)
corresponds to a functional group (H,F, Cl, Br, I, CN, SCN, NH2, N3, azomethine, thiourea-, urea-, perfluoro groups)
$R^2$ corresponds to a methyl-, ethyl-, propyl- or the corresponding perfluoro group
  an alkenyl group (vinyl-, allyl-)
  an aryl group (among others, phenyl-, tolyl-, xylyl)
  and/or aralkyl group (benzyl)
$R^3$ corresponds especially to a methyl-, ethyl-, propyl- or butyl group
  an alkylalkoxy group, preferably methylmethoxy and ethylmethoxy, or to a fatty alcohol polyglycol ether group, alkylphenolpolyglycol ether group—$CH_2CH_2$-$(O-CH_2-CH_2)_yR^4$ with y=0-25, with $R^4=C_{1-}C_{14}$-alkyl, aralkyl (benzyl, phenyl);
and alkoxysilanes of the general formula:

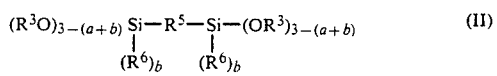

in which
$R^3$ corresponds to $R^3$ above, a=0, 1, b=0, 1
$R^6$ corresponds to a methyl-, ethyl- or propyl group
$R^5$ corresponds to an alkylene chain with $C_4-C_{20}$, preferably
  an alkenyl chain with $C_4-C_{20}$, preferably
  $(CH_2)_y$—$S_{1-8}$-$(CH_2)_y$-,

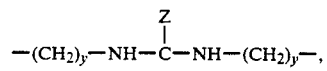

or
  -$(CH_2)_y$- NH - $(CH_2)_y$-,
  Z=O, S
  y=1-12.

Preferred examples of alkoxysilanes are: Propyltrimethoxysilane, propyltriethoxysilane, methyltrialkoxysilanes, dimethyldialkoxysilanes, phenylethyltrialkoxysilanes, hexadecyltrialkoxysilanes, cyclohexenyltrialkoxysilanes, bis(trialkoxysilyl-)alkanes, bis(methyldialkoxysilyl)-alkanes, bis(dimethylalkoxysilyl)-alkanes (alkoxy groups preferred are methoxy, ethoxy).

Suitable neutralization agents (HCl acceptor) are anhydrous ammonia, organic amines (preferably tertiary amines), basic components such as sodium alcoholates (as well as their solutions, NaOH, KOH, CaO, Ca(OH)$_2$, MgO, Mg(OH)$_2$, Na$_2$CO$_3$, CaCO$_3$, MgCO$_3$ or alkylene oxides (preferably alkylene oxide). Basic ion exchangers (e.g. REILLEX polymers 405 or 425) are preferably used since they are mostly insoluble and thermally stable in the reaction medium, bind the acid and can be readily regenerated after separation of this material.

The neutralization agents are added to the reaction medium in correspondence with the previously determined total chlorine content in equivalent molar amounts or with 0.1 to 25 mole % excess. The selection of the neutralization agent, the temperature interval, the treatment time and the amount of alcohol added takes place as a function of the functionality and structure of the alkoxysilane used.

A further advantage of this method resides in the fact that the accumulating neutralization salts can be removed and separated from the desired product mixture very simply and rapidly in a continuous manner by means of e.g. decantation using a decanter or centrifugation using a centrifuge or in a discontinuous manner e.g. by means of filtration using a Seitz pressure filter. Any suitable separation means can be used. No problems occur in the further workup steps (including the distillation). The waste chloride salt can be readily freed of adhering products by rinsing with alcohol. The return of these alcoholic solutions reduces any yield losses.

EXAMPLES

Example 1-Purification at normal pressure (analogous to EP-A-223,210)

130 kg hexadecyltrimethoxysilane (chloride content: 2.372%, alcoholic titration with silver nitrate) are placed in the reactor.

17.3 kg of a 30% sodium methylate solution (10% excess) are added. The solution is strongly alkaline, which can also be recognized from the point of change of the phenolphthalein added. The product mixture is heated up to reflux conditions and left up to 60 min. at the reflux temperature which develops. Methanol is then distilled off; a vacuum is applied for completion of the distillation, the maximum bottom temperature is approximately 120° C. After filtration, the raw product still contains 0.7% hydrolyzable chloride (or 1200 µg/g chloride, alcoholic titration with AgNO$_3$). Gas-chromatographic analysis yields a monomer content of 79.2 % by weight and a methanol content of 0.29% by weight. After distillation, the amount of hydrolyzable chloride is approximately 750 µg/g (=ppm), the hexadecyltrimethoxysilane content approximately 96.5%.

Example 2-analogous to EP-A-223,210

This example shows the further treatment analogous to the method according to EP-A 223,210 A2, example 2.
Batch:
130 kg hexadecyltrimethoxysilane (2.372% chloride)
17.3 kg NaOCH$_3$/CH$_3$OH (30%)
After the methanol has been drawn off, the addition of iron(III)chloride (ferric chloride) relative to 0.7% total chlorine content takes place. The product mixture is agitated for 60 min. only at 160° C. and then cooled off. According to gas-chromatographic analysis, the monomer content is now 70.2% by weight, the alcohol content 0.34% by weight. After the distillation the total chlorine value is 80 ppm (monomer content 95.1% by weight).

Example 3-Purification under pressure (according to the invention)

Batch:
130 kg hexadecyltrimethoxysilane (2.372% chloride)
17.3 kg NaOCH$_3$/CH$_3$OH (30%)
7.5 kg additional methanol charge Hexadecyltrimethoxysilane (acidic) is charged at room temperature into a pressure reactor. The product mixture is converted at 125° to 130° C. for 60 min.; a pressure of 4 to 6 bars builds up in the reactor. After filtration, the raw product still contains 40 µg/g (=ppm) Cl$^-$ according to alcoholic titration, the monomer content is approximately 78.8% by weight, the methanol concentration approximately 0.24% by weight. After final purification, 4 µg/g (=ppm), better <10 ppm, can be achieved as regards the hydrolyzable chloride (monomer content 97.3% by weight).

Example 4-conducted analogously to example 3

Batch:
800 g n-octyldiisopropylethoxysilane (acidic) (3.27% chloride)
242 g NaOC$_2$H$_5$/C$_2$H$_5$OH (21%)
258 g C$_2$H$_5$OH After distillation, 92.1% by weight n-octyldiisopropylethoxysilane is obtained with a chloride component of <10 ppm.

Example 5-conducted analogously to example 3

Batch:
125 kg bis(3-diethoxysilylpropyl)-monosulfane (1.75% chloride)
2.5 kg CaO
12.5 kg C$_2$H$_5$OH The raw product is treated 30 min. at 140°–145° C. After filtration, the mixture still contains 81 µg/g (=ppm) chloride. After distillation, <15 ppm can be achieved as regards the hydrolyzable chloride with a monomer content >96.2%.

Example 6-conducted analogously to example 3.

Batch:
135 kg Bis(3-triethoxysilylpropyl)-amine (1.10% chloride)
0.9 kg ammonia (liquid)
10.0 kg C$_2$H$_5$OH After the distillation, 93.7% by weight bis(-3-triethoxysilylpropyl)-amine with a chloride component of <10 ppm is obtained.

Further variations and modifications of the invention will become apparent to those skilled in the art from the foregoing and are intended to be encompassed by the claims appended hereto.

German Priority Application P 41 30 643.0, filed on Sep. 14, 1992, is relied on and incorporated by reference.

What is claimed:
1. A method of purifying alkoxysilanes of hydrolyzable chlorine atoms, comprising reacting said alkoxysi- lanes in a pressure reactor with an alcohol, optionally in the presence of an HCl acceptor, at a temperature of 5° C. to 160° C. and at the pressure which develops thereby to form purified alkoxysilanes containing less than 15 μg/g hydrolyzable chloride.

2. The method according to claim 1, wherein said temperature is 40 to 70° C. above the boiling point of said alcohol.

3. The method according to claim 1, wherein said alcohol corresponds to the alkoxy groups on the Si atom of said alkoxysilane.

4. The method according to claim 1, wherein the concentration of said alcohol is equivalent to the amount of Cl atoms to be hydrolyzed.

5. The method according to claim 1, wherein said alkoxysilane has the formula
wherein n=0, 1, or 2, wherein a=0 or 1, and
- $R^1$ is selected from the group consisting of an alkylene group with a chain length of $C_3$-$C_{20}$, an alkenylene group, an arylene group, and an aralkyl group;
- X comprises a functional group (H, F, Cl, Br, I, CN, SCN, NH, N, azomethine, thio urea, irea or perfluoro groups;
- $R^2$ is selected from the group consisting or a methyl-, ethyl-, propyl- or the corresponding perfluoro group, an alkenyl group, an aryl group, and an aralkyl group;
- $R^3$ is selected from the group consisting of a methyl-, ethyl-, propyl- or butyl group, an alkylalkoxy group, a fatty alcohol polyglycol ether group, and an alkylphenolpolyglycol ether group having the formula $CH_2CH_2$-$(OCH_2$-$CH_2)_yR^4$ wherein y=0-25 and $R^4$ is $C_1$-$C_{14}$-alkyl or aralkyl.

6. The method according to claim 5, wherein
- $R^1$ is vinylene, propylene, phenylene, tolyl, xylyl, or benzyl;
- X is H, F, Cl, Br, I, CN, SCN, $NH_2$, $N_3$, azomethine, thiourea, urea, or perfluoro groups;
- $R^2$ is vinyl, allyl, phenyl, tolyl, xylyl, or benzyl;
- $R^3$ is methylmethoxy or ethylethoxy; and $R^4$ is $C_1$-$C_{14}$ benzyl or phenyl.

7. The method according to claim 1, wherein said alkoxysilane has the formula

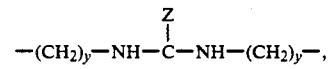         (II)

wherein a=0 or 1, b=0 or 1, and
- $R^3$ is selected from the group consisting of a methyl-, ethyl-, propyl- or butyl group, an alkylalkoxy group, a fatty alcohol polyglycol ether group, and an alkylphenolpolyglycol ether group having the formula $CH_2CH_2$-$(O$-$CH_2$-$CH_2)_yR^4$ wherein y=0-25 and $R^4$ is $C_1$-$C_{14}$-alkyl or aralkyl;
- $R^6$ is a methyl-, ethyl- or propyl group;
- $R^5$ is an alkylene chain with $C_4$-$C_{20}$.

8. The method according to claim 7, wherein $R^5$ is an alkenyl chain with $C_4$-$C_{20}$.

9. The method according to claim 8, wherein
$R^5$ is -$(CH_2)_y$-$S_{1-8}$-$(CH_2)_y$-,

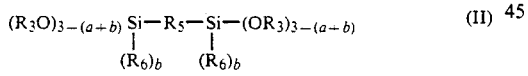

or -$(CH_2)_y$- NH - $(CH_2)_y$-; Z is 0 or S, and y=1 to 12.

10. The method according to claim 1, wherein said alkoxysilanes is selected from the group consisting of propyltrimethoxysilane, propyltriethoxysilane, methyltrialkoxysilanes, dimethyldialkoxysilanes, phenylethyltrialkoxysilanes, hexadecyltrialkoxysilanes, cyclohexenyltrialkoxysilanes, bis(trialkoxysilyl-)alkanes, bis(methyldialkoxysilyl)-alkanes, and bis(dimethylalkoxysilyl)-alkanes.

11. The method according to claim 10, wherein said alkoxy component is methoxy or ethoxy.

12. The method according to claim 1, wherein said HCl acceptor is selected from the group consisting of anhydrous ammonia, organic amines, sodium alcoholates, NaOH, KOH, CaO, Ca(OH)$_2$, MgO, Mg(OH)$_2$, Na$_2$CO$_3$, CaCO$_3$, MgCO$_3$, alkylene oxides, and basic ion exchangers.

13. The method according to claim 12, wherein said organic amines are tertiary amines.

14. The method according to claim 12, wherein said HCl acceptor is a basic ion exchanger.

15. The method according to claim 4, wherein said concentration of said alcohol is 5 to 40% by weight relative to the total mixture.

16. The method according to claim 1, wherein said HCl acceptor is present in equivalent molar amount as the chlorine content or up to 0.1 to 25 mole% excess.

17. The method according to claim 1, wherein said pressure is 1 to 50 bars.

18. The method according to claim 1, further comprising separating a chloride salt formed.

19. The method according to claim 18, wherein said separating is carried out by decantation, centrifugation or filtration.

* * * * *